United States Patent [19]

Klesius et al.

[11] Patent Number: 4,878,895
[45] Date of Patent: Nov. 7, 1989

[54] IN-VIVO STIMULATION, COLLECTION, AND MODIFICATION OF PERITONEAL MACROPHAGE

[75] Inventors: Phillip H. Klesius; Debra A. Cross, both of Auburn, Ala.

[73] Assignee: The United States of America as represented by the Secretary of Agriculture, Washington, D.C.

[21] Appl. No.: 248,744

[22] Filed: Sep. 26, 1988

[51] Int. Cl.[4] ........................ A61M 1/00; A61B 10/00
[52] U.S. Cl. .................................... 604/49; 128/769; 128/899
[58] Field of Search ................. 604/49, 6, 29, 93, 317, 604/328; 128/769, 749, 760, 899

[56] References Cited

U.S. PATENT DOCUMENTS

| | | | |
|---|---|---|---|
| 3,313,289 | 4/1967 | Kapral | 128/1 |
| 3,924,607 | 12/1975 | Bucalo | 128/769 |
| 4,217,889 | 8/1980 | Radovan et al. | 128/1 R |
| 4,301,814 | 11/1981 | Sneer | 128/769 |
| 4,364,394 | 12/1982 | Wilkinson | 604/96 |
| 4,505,277 | 3/1985 | Klesius et al. | 128/769 |
| 4,732,155 | 3/1988 | Zetter et al. | 128/769 |

OTHER PUBLICATIONS

"RADOVAN TM Tissue Expander", Mentor Corp., Goleta, CA, 102383-002-01, Jan. 1987.
Hayashi, Hideo et al., "Characterization and Functional Specifity ... ", Macrophage Biology, p. 231-245, 1985, Alan R. Liss, Inc.
Kambara, Takeshi et al., "Chemotactic Factors for Macrophages ... ", Macrophage Biology, pp. 271-284, Alan R. Liss, Inc.
"Harvest of White Blood Cells", Science News, p. 88, vol. 129 (6), Feb. 8, 1986.
Klesius et al., "An Implantation Chamber ... ", The Ruminant Imm. Sys. Adv. in Exp. Med. and Bio., edited by J. E. Butler et al., Plenum Press, NY, pp. 773-774, 1981.
Veale, D. R. et al., "Differential Ability of Colonial Types ... ", J. Med. Microbiol., vol. 8, pp. 325-335, 1975.
Shelton, Emma et al., "Growth of Normal Peritoneal Cells ... ", The Am. J. of Anatomy, pp. 281-341, vol. 105, No. 3, Nov. 1959.
Stuart, A. E. et al., "Phagocytes in vitro", pp. 24.1-24.3, Handbook of Experimental Immunology, 2nd Ed., D. M. Weir editor, Blackwell Scientific Publications, Oxford, England, 1976.
Lotz, M. et al., "Effects of Neuropeptides on Production of Inflammatory ... ", Science, vol. 241, pp. 1218-1220, 2/9/88.

Primary Examiner—Stephen C. Pellegrino
Attorney, Agent, or Firm—David R. Sadowski; M. Howard Silverstein

[57] ABSTRACT

The instant invention pertains to improvements in processes and apparatus for stimulating, collecting, and optionally modifying, macrophages from the peritoneal cavity of a vertebrate.

24 Claims, 3 Drawing Sheets

IN-VIVO STIMULATION, COLLECTION, AND MODIFICATION OF PERITONEAL MACROPHAGE

BACKGROUND OF THE INVENTION

1. Field Of The Invention

The present invention is drawn to, improvements in apparatus and processes for stimulating, collecting, and optionally modifying macrophages (for example monocytes) from the peritoneal cavity of a vertebrate, as well as highly novel and inventive relative processes and apparatus.

2. Description Of The Prior Art

U.S. Pat. No. 4,505,277 issued 3/19/85 to Klesius et al, describes a device for in-vivo stimulation and collection of monocytes from the peritoneum of vertebrates. While this device has proven to be effective, it has unexpectedly and surprisingly been discovered that certain improvements as set forth herein may be made to such a device.

SUMMARY

A first aspect of the present invention relates to providing, within an implantation device for stimulation and collection of macrophages (e.g. monocytes) from the peritoneal cavity of vertebrates, cell supporting means (CSM). Said cell supporting means provide an increased surface upon which macrophages may attach and optionally grow. The macrophages may subsequently be removed from the CSM using a detachment solution.

Another aspect of the present invention relates to providing within such a device macrophage attractants or chemotactic factors, as for example by associating said attractants or factors with CSM.

Another aspect of the present invention pertains to a macrophage collector including: container means consisting essentially (e.g. solely) of membrane means, completely enclosing therein an interior volume, for excluding tissue growth into the interior volume and for permitting permeation of macrophage through said membrane means into said interior volume; and cell supporting means in said interior volume. Thus, precluding additional container means such as the container designated 1 in U.S. Pat. No. 4,505,277, and thereby advantageously and unobviously simplifying the construction of the collector.

Another aspect of the present invention relates to, removal of macrophages from such a device, in-vitro antigen priming (i.e. arming) of the collected macrophages to arm them against particular antigen(s), with subsequent local or system introduction of the armed macrophages into the same or different vertebrate to present this antigen to the lymphocytic population with resultant interaction to provide immunity.

Another aspect of the present invention relates to an inventive and highly advantageous overall macrophage collector configuration including, a substantially rectangular outwardly convex front sealingly joined to: two rectangularly shaped ends, and two sides each having the same shape of an arched band; and a substantially rectangular inwardly concave back (having generally the same shape as the front) which is substantially parallel to the front and sealingly joined to said ends and sides; wherein said front and sides each define a plurality of apertures.

Another aspect of the present invention relates to preventing undesirable concentrating or pooling of macrophage in the corners of a collector by provision of flow directing means. Such flow directing means may for example take the form of shoulders, which provide efficient and advantageous directing of macrophage.

Other aspects and advantages of the present invention will become readily apparent from the ensuring description.

DESCRIPTION OF THE PREFERRED EMBODIMENTS

Figure 1:
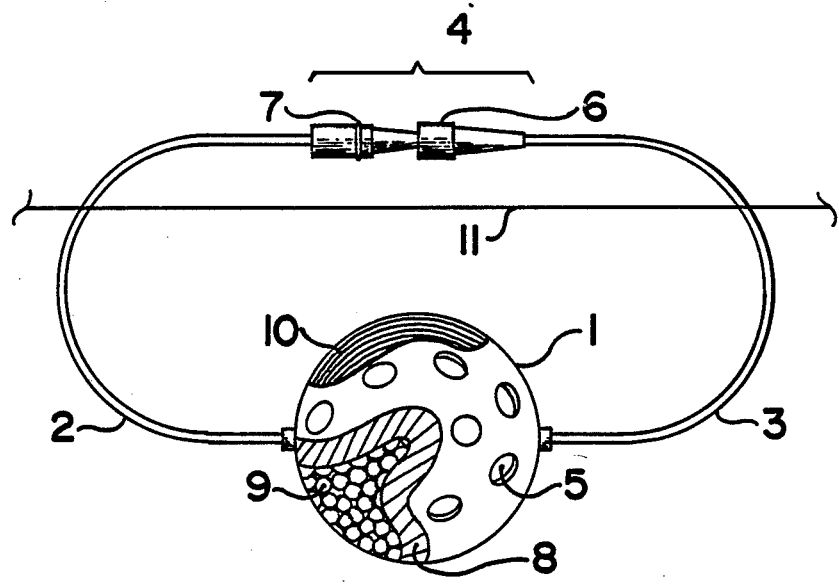
FIG. 1 is a partially cut away front view of an apparatus of the present invention, connected to couplings positioned exteriorly of a vertebrate.
Figure 2:
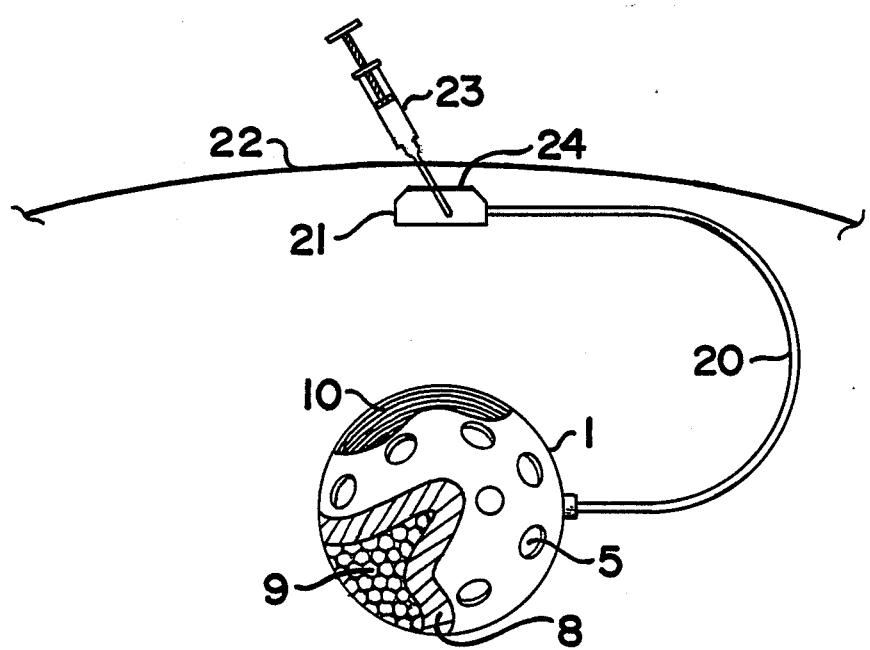
FIG. 2 is a partially cut away front view of an apparatus of the present invention, connected to a subcutaneous injection reservoir.
Figure 3:
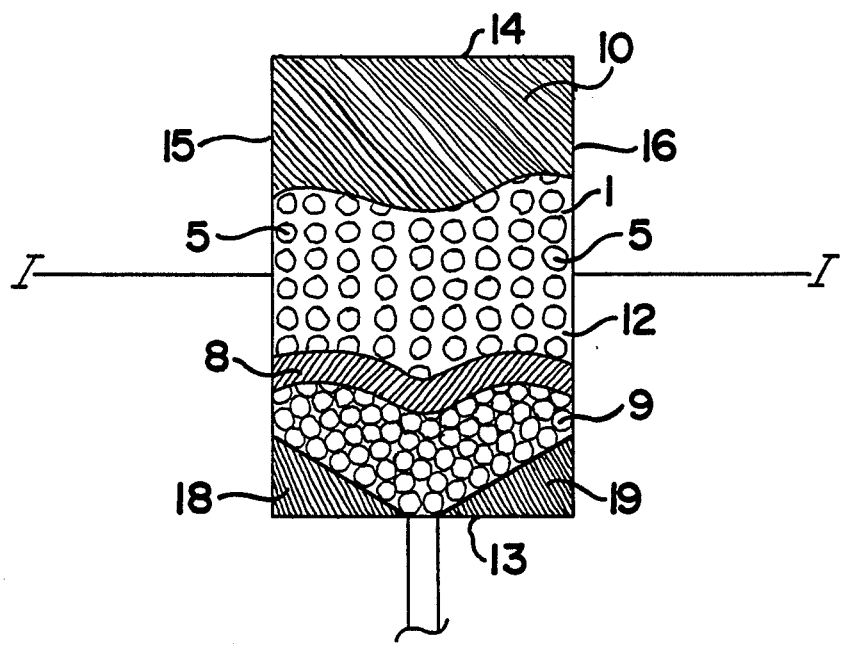
FIG. 3 is a top view of a partially cut-away macrophage collector of the present invention.
Figure 4:
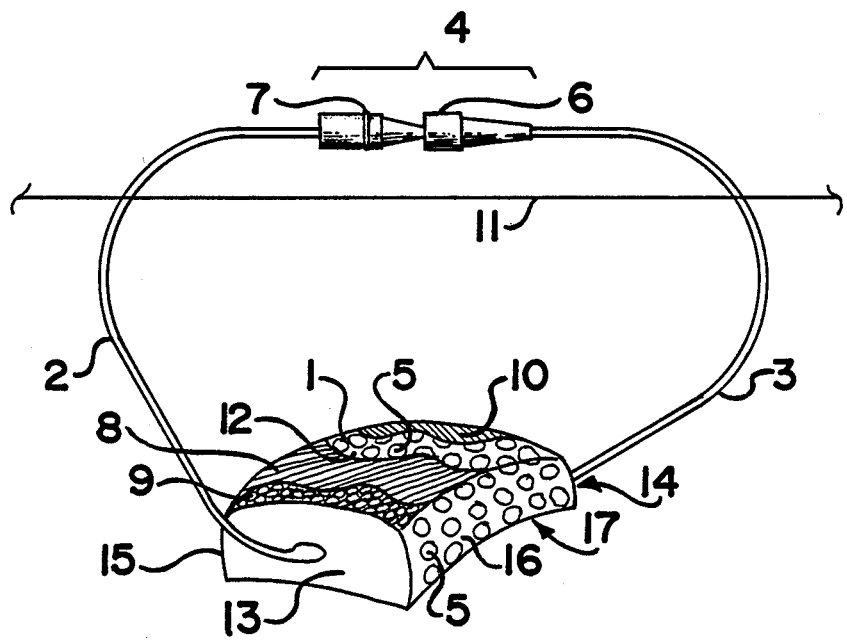
FIG. 4 includes, a partially cut-away, perspective end view of the collector of FIG. 3, connected to couplings positioned exteriorly of a vertebrate.

Attention is first directed to the macrophage collector shown in each of FIGS. 1-6. Each collector includes container means which may, include or consist essentially of or consist solely of, membrane means 10 (defining therein an interior volume), which may be of any convenient:

(1) configuration e.g. spherical as shown in FIGS. 1 and 2, disc shaped, cylindrical, rectangularly cross-sectioned and arched as shown in FIGS. 3-6 to provide ease of implantation and to fit against the peritoneum (i.e. including, an outwardly convex substantially rectangular front 12, which defines at least one aperture and is sealingly joined to both: (a) two ends 13 and 14 of substantially rectangular shape (ends 13 and 14 both having substantially the same shape), and (b) two sides 15 and 16 having the shape of arched bands (sides 15 and 16 both having the same shape) and each defining at least one aperture;

and a substantially rectangular inwardly concave back 17 (having substantially the same shape as the front 12) which is substantially parallel to the front and sealingly joined to the ends 13 and 14 and to the sides 15 and 16);

(2) material or composition i.e. any biocompatible material compatible for implantation into a vertebrate, such as, nylon stockings, panty hose, filter material, porous (e.g. woven or mesh) material (such as latex, silk, plastic (e.g. polypropylene, nylon) aluminum or stainless steel, glass, ceramic), commercially available membranes defining pore diameters which permit permeation of macrophage while excluding tissue in growth, etc.;

(3) size i.e. adjusted to suit the size of the peritoneal cavity of the vertebrate into which the device is implanted, for example, the outer diameter of a spherical collector for implantation into; a calf, may be about 4.2 centimeters (cm) (1 21/32 inches), and for a human about 5 cm (2 inches): while a collector of the configuration shown in FIGS. 3 to 6 for implantation into; a calf, may be about 5 cm wide by 8 cm long (measured from one end of the front portion to the other end of the front portion); a human, may be about 4 cm wide by about 6 cm long.

Said membrane means must, permit permeation of macrophage through the membrane means and into the interior volume, while excluding tissue growth into the housing. The membrane means 10 may be sufficiently rigid to resist collapse while implanted in a peritoneal cavity and thereby maintain therein a relatively, large unoccupied interior volume. Alternatively, membrane means 10 may be relatively flexible, and thereby be pressed against cell supporting means 9 while implanted in a peritoneal cavity, thus at least partially relying upon the cell supporting means to maintain an interior volume therein. In the accompanying drawings, the major portion of the membrane means 10 is broken away in order to reveal the components therein. Optionally the container means may include a housing 1 which may provide additional rigidity or strength. The housing 1 defines at least one aperture (e.g. a plurality of apertures) designated 5, which may be of any convenient size or shape. The collector housing illustrated in FIGS. 3-6 defines apertures 5 in its front and two sides. The housing 1 may be constructed with configurations and compositions such as those useable for the membrane means (e.g. nylon, latex, silk, polypropylene, aluminum, stainless steel, glass, ceramic, etc.) but is nonporous (other than apertures 5) and thus impermeable to tissue ingrowth other than through apertures 5. The membrane means 10 may extend across and in fluid tight sealing relationship with all of the apertures 5 e.g. (a) covering the entire exterior of the housing 1, or (b) covering only the front and sides of the collector shown in FIGS. 3-6. Alternatively, the membrane means, may extend over and/or on the entire interior surface of the housing, or may take the form of a plurality of individual separate membranes each of which is in sealing relationship with one aperture 5. Consequently, the housing and membrane means cooperate to exclude tissue growth into the interior volume. In order to permit permeation of macrophage and exclude tissue in growth, the membrane means will typically define pore diameters of about 6 to about 20 microns, preferably about 8 to about 16 microns, and most preferably about 8 microns. It has been discovered to be highly advantageous to provide within the membrane means 10 cell supporting means (CSM) designated 9, which while shown for purposes of illustration in FIGS. 1-5 as spheres, may be of any convenient configuration (e.g. one or more of: beads or pellets designated 30 in FIG. 6; grid(s) or grill(s) or plural rods designated 31 in FIG. 6; oriented or random fibers designated 32 in FIG. 6; and/or cylinders designated 33 in FIG. 6) and material which provides surface area upon which macrophages may attach and optionally grow. Provision of CSM within the device permits collection of larger numbers of macrophages then would be possible without the CSM, by providing increased surface area for attachment of cells and cell reproduction within the device. The degree to which the interior volume is occupied by the CSM may be adjusted as desired, e.g. 50% of the interior volume may be occupied by the CSM. As illustrated in the drawing figures, the CSM 9 may optionally be contained in an interior membrane means 8, which may be of a membrane material as described herein above in regard to the membrane means 10, and therefore is permeable to macrophage but impermeable to tissue ingrowth. Materials which may be utilized as the CSM include: porous or nonporous beads consisting essentially of glass or plastic, spheres or microspheres e.g. composed of a chemically fixed collagen material (such microspheres are commercially available as "Microcarrier" available from Chemap AG, Switzerland/8604 Voldetswil, or Chemap Inc., South Plainfield, N.J.); soluble materials of e.g. polyacrylamide or a soluble matrix having combined therewith a chemotactic substance i.e. chemotactic factor(CF); insoluble materials of e.g. glass, plastic (e.g. polystyrene), etc. having absorbed or adsorbed thereon or therein chemotactic factor(CF); a hollow CSM containing therein chemotactic factor; materials which are capable of absorbing or adsorbing chemotactic factors and thereby permit in-vivo combining of the CSM with the CF (e.g. to permit, initial charging of the CSM with CF after implantation of the device, or regeneration of the CSM with additional CF if dissipation of the CF occurs after a period of use).

Macrophage chemotactic substances (i.e. chemotactic factors) which may be utilized in the present invention include;

(A) Infectious agent-derived substances, i.e, chemotactic substances from bacteria, parasites, fungi or viruses that cause macrophage accumulation. These substances may be toxins, antigens, lectins, excretory or secretory substances or components of infectious agents. For example, bacterial culture fluids from *E. coli., Pneumococcus, Corynebacteria, Mycobacterium;* Ascaris extract and other similar substances from parasites and fungi.

(B) Cell-derived chemotactic substances that are produced in response to infectious agents, inflammatory molecules, mitogens, antibody-antigen reactions or serum component activation. Broadly these cell categories are:

(1) Thymus-dependent lymphocytes (T-cells).

(2) Leukocytes such as monocytes and granulocytes.

(3) Accessory cells—mast, dermal, respiratory and intestinal cells. For example, lymphokines, monokines and cytokines; a transfer factor, platelet factor 4, fibroblasts, smooth muscle, virus infected cells and tumor cells derived substances.

(c) Serum-derived chemotactic substances such as activated complement components, antibody and inflammatory components. For example, normal serum, IgG derived, complement fragment, C5a; plasminogen activator, fibrinopeptides, a-Thrombin, and fibronectin fragments. Other examples, are extracellular molecules such as collagen and fragments, casein, bone-derived and elastic fragments.

(D) Synthetic chemotactic substances that mimic natural products with chemotactic activity.

Such chemotactic factors are referred to in: T. R. Kambara et al "Chemotactic Factors for Macrophages Produced In Vivo", pages 271-284 and H. Hayashi et al "Characterization and Functional Specificity of Macrophage Chemotactic Factors in Inflammation" pages 231-245, both in *Macrophage Biology*, 1985, Alan R. Liss, Inc. N.Y., N.Y..

One of ordinary skill in the art would be capable of selecting an appropriate chemotactic factor(s) from the above list depending on e.g. the species of vertebrate from which the macrophage is to be collected.

The macrophage collectors of the present invention may be utilized without conduits or external connections i.e. the macrophage may be removed from the collector by inserting a hypodermic needle through the skin of the vertebrate directly into the collector, and withdrawing the macrophage from the collector directly i.e. the membrane means and/or housing being puncturable by the hypodermic needle. Alternatively, other means may be employed for withdrawing macrophage from the collector, such as those illustrated in FIGS. 1, 2, 4 and 5. In the embodiments shown in FIGS. 1 and 4, the means for withdrawing macrophages includes, inlet conduit 2 and outlet conduit 3 both of which are: in fluid tight sealed relationship with the membrane means, and in communication with the interior volume. The terms "inlet" and "outlet" are utilized for purposes of illustration only, as either conduit may function as an inlet or outlet. The ends of conduits 2 and 3 distal from the collector, are provided with a quick disconnect coupling designated 4, including a female adapter 6 and a male adapter 7. This coupling allows quick connection or disconnection of the adapters. When in position for use, the collector and portions of the conduits 2 and 3 are within the peritoneal cavity of the vertebrate, while the coupling 4 and portions of conduits 2 and 3 extend exteriorly of the vertebrate skin designated 11 (i.e. extracorporeally) in FIGS. 1 and 4. In use, the adapters would normally be, interconnected (i.e. interfitted) or capped or plugged, inorder to retain fluid within the device and maintain a sterile environment therein. Inorder to recover macrophage with the macrophage withdrawing means of FIG. 1: (1) the adapters 6 and 7 are disconnected from each other; (2) a syringe containing a macrophage detachment solution (e.g. heprinized saline solution, or a solution containing enzymes (for example, 5 grams Trypsin and 2 grams EDTA in one liter of sterile one normal saline solution), or LID O CAIN TM solution), is connected to male adapter 7; (3) a sterile tube or syringe is connected to female adapter 6; (4) the detachment solution is forced from the syringe, through male adapter 7, conduit 2, flushing the macrophage from housing 1 though outlet conduit 3, and out of adapter 6, so that a mixture of detachment solution and macrophage is received in the sterile tube or syringe.

Figure 5:
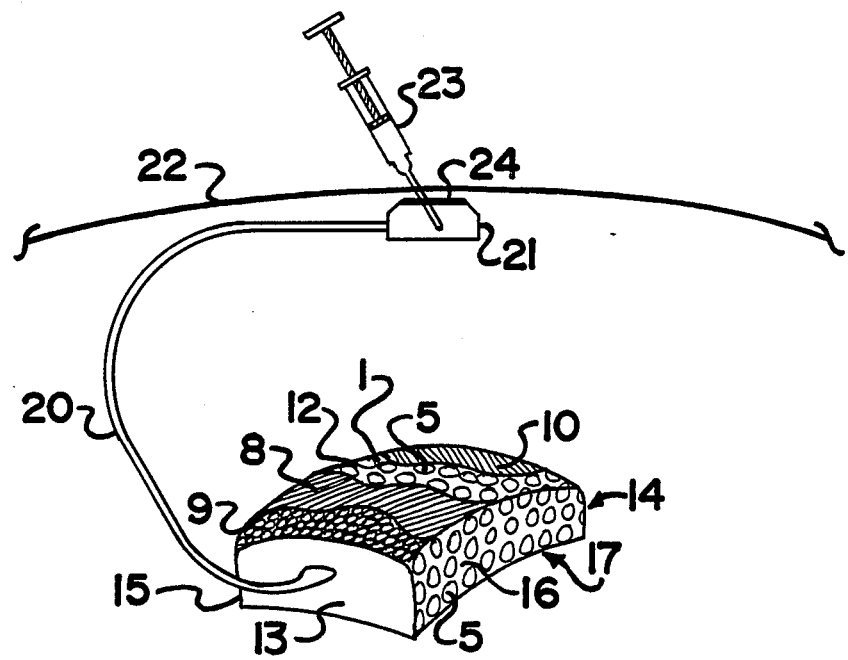
FIG. 5 includes, a partially cut-away, perspective end view of the collector of FIG. 3, connected to a subcutaneous injection reservoir.
Figure 6:
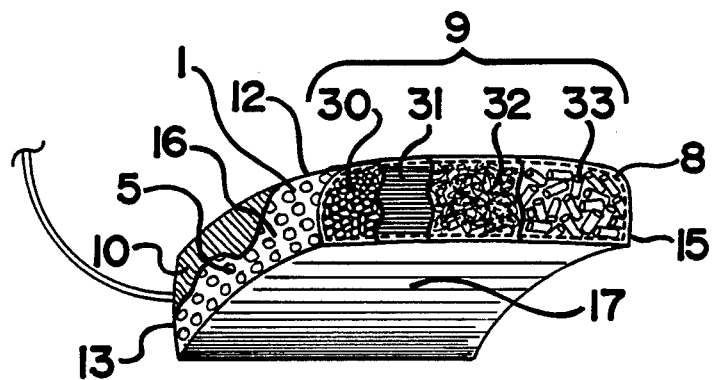
FIG. 6 shows a cross-section of the macrophage collector of FIG. 3 cut along line I-I.

In the embodiment shown in FIGS. 2 and 5 the means for withdrawing macrophages includes a conduit 20, in fluid tight sealed relationship with and communicating with the interior of, both housing 1 and injection reservoir 21. The injection reservoir 21 is implanted in the vertebrate immediately below the dermis 22. At least a portion of the injection reservoir 21 is made of a material 24 which is puncturable by a hollow needle and self sealing to a track of a hollow needle. Such an injection reservoir may for example be the commercially available injection reservoir utilized with the RADOVAN TM tissue expander available from the Mentor Corp. Goleta Calif. and described in U.S. Pat. No. 4,217,889 issued August 19, 1980 to Chedomir Radovan et al. The following procedure may be utilized to remove macrophage with the macrophage withdrawing means of FIGS. 2 and 5: (1) the needle of a hypodermic syringe 23 containing a heparinized saline solution is inserted through the skin of the vertebrate and into the self sealing puncturable portion 24 of the injection reservoir 21; (2) the plunger of the hypodermic syringe 23 is repeatedly reciprocated inorder to move solution into and out of the reservoir 21, conduit 20 and housing 1, so as to flush macrophage from the CSM 9 into the solution; (3) the combined solution and macrophage are then drawn into the hypodermic syringe, and the needle is withdrawn from both the injection reservoir and the vertebrate. In this regard, it has been found that the macrophage may concentrate or pool in the corners of the device thereby hindering their removal. It has been discovered that in order to avoid this problem, and provide more efficient removal of the macrophage from a collector of the shape shown in FIGS. 3–6, the collector may be provided with flow directing means, such as shoulders (liquid and macrophage impermeable) designated 18 and 19 in FIG. 3. The shoulders 18 and 19: are both of substantially the same configuration; are positioned adjacent the ends of the collector; and are each tapered from a relatively large thickness at a portion adjacent the side of the collector (i.e. remote from the conduit) to a relatively small thickness at a portion of each said shoulder adjacent a conduit which is in fluid tight sealed relationship to a central portion of one of said ends. Thus, the shoulders each define a right triangular cross-section. Said shoulders function to direct macrophage more directly to the conduit and thereby prevent macrophage from concentrating or pooling in the corners of the collector. Said flow directing means permits more efficient removal of the macrophage from the collector.

The entire device may be made to be disposable, so that it may be discarded after removal from the vertebrate. The device should of course be sterilized prior to implanting within the vertebrate. This may for example be accomplished in a well known manner by treating the device with radiation or gas subsequent to packaging (e.g. in suitable plastic, paper, cellulose-type wrapper, etc.). The device may be safely removed from the vertebrate without endangering its health.

Another aspect of the present invention relates to use of peritoneal macrophage collection, with in-vitro antigen priming or arming to specifically arm the macrophages against particular antigen(s) (i.e. to provide an altered state of immune reactivity), and subsequent intravenous introduction or reintroduction of the armed macrophages to present the antigen(s) to the lymphocytic populations, whereby the resultant interactions will provide immunity. The peritoneal macrophage may for example be armed or primed by: (a) coculturing the macrophage with at least one antigen for which the macrophage is to be armed or primed; (b) coculturing the macrophage with at least one monocyte activator e.g. lipopolysaccharide, neuropeptides (such as those discussed in M. Lotz et al "Effect of Neuropeptides on Production of Inflammatory Cytokines by Human Monocytes", Science, Vol. 241, p. 1218–1220, Sept. 2, 1988, etc., subsequent local or systemic introduction of monocyte activator primed macrophages into the same or different vertebrate will provide regulation of cellular functions related to inflammation and immunological responses; or (c) gene transfer in-vitro (i.e. genes that code for an antigen(s) may be transferred to macrophages obtained from a collector). For example, for treatment of neoplasia, neoplastic cells maybe cocultured with monocytes collected from a monocyte collector (e.g. a collector as described in U.S. Pat. No. 4,505,277 to Klesius et al, or a collector constructed in accordance with the present invention). The cultured monocytes are tested for, altered reactivity or priming, to the neoplastic cells by determining their function with migration inhibition, cellular, or soluble assays.

The in-vitro antigen-primed monocytes are then introduced or reintroduced (locally or systemically) into a vertebrate to activate components of the immune system to attack the neoplastic cells. Also, for those vertebrates in need of immunosuppression (e.g. organ transplant recipients, or vertebrates suffering from altered immune reactivity such a Lupus or other diseases where the immune system works against itself or the individual) monocytes collected from the monocyte collector by: (a) inserting a needle through the skin directly into the collector and flushing with heparin saline using a syringe, or; (b) by the use of the inlet and outlet tubes as previously described. The collector was flushed with 15 milliliters (ml) of sterile saline 9 days after implantation. Two micrograms of the chemotactic factor PHA (i.e. phytohemagglutinin) in 2 ml of saline was injected into the collector 11 days after implantation. The results are shown in table 1.

TABLE 1

| Days after Implantation | TOTAL No. of White Blood Cells Collected* | Percentage of the total cells collected which were | | |
|---|---|---|---|---|
| | | Polymorpho-nuclear cells | Macrophage | Lymphocyte |
| 16 | 522,000 | 75 | 24 | 1 |
| 19 | 1,541,500 | 77 | 22 | 1 |
| 23 | 2,650,000 | 65 | 35 | 0 |
| 30 | 8,500,250 | 40 | 59 | 1 |
| 33 | 5,600,430 | 47 | 52 | 1 |
| 40 | 10,940,020 | 42 | 53 | 5 |
| 42 | Experiment was terminated. | | | |

*0.5% by volume trypsin solution was used to collect cells on day 19 and 23, and a 0.9% by volume LID O CAIN ™ solution was used to collect cells on days 30, 33, and 40.

and antigen primed in-vitro may be used to suppress components of the immune system upon their introduction or reintroduction into a vertebrate.

it is understood that the foregoing detailed description is given merely by way of illustration and that modification and variations may be made therein without departing from the spirit and scope of the invention.

EXAMPLE

The following example is intended only to further illustrate the invention and is not intended to limit the scope of the invention which is defined by the claims.

The collector used in the present example was generally of the structure described in the example in U.S. Pat. No. 4,505,277 issued Mar. 19, 1985 to Klesius et al i.e. including a spherical container of white translucent semi-flexible nontoxic nonpyrogenic implantable and blood compatible polypropylene with, a 1 21/32 inch outer diameter, a 1 17/32 inch inner diameter, a 2/32 inch wall thickness, and defining 24 holes each of 7/32 inch diameter. Said container was fitted with two tubes and covered with a nylon stocking. However, the collector was modified, in that about 50% of its interior volume was occupied by glass spheres of approximately 0.3 to 0.6 cm diameter. The process utilized for surgically implanting the collector within a calf was as follows. The calf was treated with 5 cubic cm of COMBIOTIC ™ by daily intramuscular injections. A 10 cm vertical incision was made in the right paralumbar fossa, and the underlying fascia and muscle were bluntly dissected and cut to expose the peritoneum. Two holes were made at 11 and 1 o'clock positions through the dermis, fascia and muscle about 30–40 cm dorsal to the incision. The two tubes of the collector were pulled through the holes to the outside and sutured in place over the backbone. The collector was placed in a pocket (below the edge of the incision) directly next to the peritoneum and medial to the overlying fascia and muscle layers. The tubes of the collector were flushed with sterile saline before the collector was placed in the pocket. The muscle and fascial layers were closed in a continuous pattern with absorbable suture. The skin was closed with a Ford interlocking suture pattern using non-absorbable VETAFIL ™ suture material. Macrophages were collected from the collector either

INDEX OF APPARATUS ELEMENTS DESIGNATED BY A NUMERAL

| | |
|---|---|
| 1. housing | 17. collector back |
| 2. inlet conduit | 18. shoulder |
| 3. outlet conduit | 19. shoulder |
| 4. complementary quick disconnect couplings | 20. conduit |
| 5. apertures | 21. injection reservoir |
| 6. female adapter | 22. dermis |
| 7. male adapter | 23. hypodermic syringe |
| 8. interior membrane means | 24. puncturable self sealing material |
| 9. cell supporting means (CSM) | 30. beads or pellets |
| 10. membrane means | 31. grid/grill/rods |
| 11. skin | 32. fibers |
| 12. outwardly convex front | 33. cylinders |
| 13. collector end | |
| 14. collector end | |
| 15. collector side | |
| 16. collector side | |

We claim:

1. An apparatus for collection of macrophage from the peritoneal cavity of a vertebrate including,
   container means consisting essentially of membrane means, completely enclosing therein an interior volume, for excluding tissue growth into said interior volume and for permitting permeation of macrophage through said membrane means into said interior volume, and
   cell supporting means filling at least a portion of said interior volume.

2. An apparatus for collection of macrophage from the peritoneal cavity of a vertebrate including:
   container means including: a housing of a material which is impermeable to tissue ingrowth and defining at least one aperture; membrane means, sealing fluid tight said at least one aperture whereby said housing and membrane means cooperate to completely enclose therein an interior volume, for excluding tissue growth through said at least one aperture into said interior volume and for permitting permeation of macrophage through said membrane means into said interior volume, whereby said housing and said membrane means cooperate to exclude tissue growth into said interior volume; and cell supporting means filling at least a portion of said interior volume.

3. The apparatus of claim 2 further including a macrophage permeable interior membrane means within said interior volume, said interior membrane means encompassing said cell supporting means.

4. The apparatus of either claim 1 or 2 further including a conduit, in fluid tight sealed relationship to said membrane means, and in fluid communication with said interior volume.

5. The apparatus of claim 4 further including an injection reservoir in fluid tight sealed relationship to said conduit, said injection reservoir having at least a portion thereof puncturable by a hollow needle and self sealing to a track of a hollow needle.

6. The apparatus of either claim 1 or 2 further including two conduits, each in fluid tight sealed relationship to said membrane means, and each in fluid communication with said interior volume.

7. The apparatus of claim 6 wherein a first of said conduits is connected to a female adapter, and a second of said conduits is connected to a male adapter interfittable into said female adapter.

8. The apparatus of either claim 1 or 2 wherein said container means is spherical.

9. The apparatus of either claim 1 or 2 wherein said container means has, a substantially rectangular outwardly convex front which defines at least one aperture, and is sealingly joined to both: two rectangularly shaped ends; and to two sides each having the shape of an arched band, said two sides each defining at least one aperture, and a substantially rectangular inwardly concave back which is sealingly joined to said ends and sides.

10. The apparatus of claim 9 further including, a conduit in fluid tight sealed relationship to a central portion of a first of said ends, and flow directing means including two shoulders each tapered from, a relatively large thickness at a portion of each shoulder adjacent a said side, to a relatively small thickness at a portion of each said shoulder adjacent said conduit.

11. The apparatus of either claim 1 or 2 further including a chemotactic substance combined with said cell supporting means.

12. The apparatus of either claim 1 or 2 wherein said cell supporting means comprises a plurality of spheres.

13. The apparatus of either claim 1 or 2 wherein said cell supporting means is of a material selected from the group consisting of glass, plastic or chemically fixed collagen.

14. The apparatus of either claim 1 or 2 wherein said membrane means defines pore diameters of about 6 to about 20 microns.

15. The apparatus of claim 14 wherein said membrane means defines pore diameters of about 8 to about 16 microns.

16. The apparatus of claim 15 wherein said membrane means defines pore diameters of about 8 microns.

17. A process for collection of macrophage from the peritoneal cavity of a vertebrate comprising, implanting within the peritoneal cavity of a vertebrate the apparatus of claim 1, permitting macrophage to permeate through said membrane means into said interior volume, and removing the permeated macrophage from said interior volume externally of said vertebrate 18. A process for collection of macrophage from the peritoneal cavity of a vertebrate comprising, implanting within the peritoneal cavity of a vertebrate the apparatus of claim 2, permitting macrophage to permeate through said membrane means into said interior volume, and removing the permeated macrophage from said interior volume externally of said vertebrate.

19. The process of claim 18 wherein said collector apparatus includes a macrophage permeable interior membrane means within said interior volume, said interior membrane means encompassing said cell supporting means.

20. The process of either claim 17 or 18 further including, antigen priming the removed permeated macrophage to arm the macrophage against at least one antigen, and introducing the antigen primed macrophage into a vertebrate.

21. The process of claim 20 wherein said antigen priming is selected from the group consisting of, coculturing the removed permeated macrophage with at least one antigen or transferring at least one gene to the removed permeated macrophage.

22. The process of either claim 17 or 18 further including the step of combining a chemotactic substance with said cell supporting means.

23. A process comprising, implanting within the peritoneal cavity of a vertebrate a macrophage collector means, collecting macrophage within said macrophage collector means, removing macrophage from said macrophage collector, means externally of said vertebrate, antigen priming the removed macrophage to arm the removed macrophage against at least one antigen, and introducing the antigen primed macrophage into a vertebrate.

24. The process of claim 23 wherein said antigen priming is selected from the group consisting of, coculturing said removed macrophage with at least one antigen, coculturing said removed macrophage with at least one monocyte activator, or transferring at least one gene to said removed permeated macrophage.

* * * * *